US006531121B2

(12) United States Patent
Brines et al.

(10) Patent No.: US 6,531,121 B2
(45) Date of Patent: Mar. 11, 2003

(54) PROTECTION AND ENHANCEMENT OF ERYTHROPOIETIN-RESPONSIVE CELLS, TISSUES AND ORGANS

(75) Inventors: Michael Brines, Woodbridge, CT (US); Anthony Cerami, Sleepy Hollow, NY (US); Carla Cerami, Sleepy Hollow, NY (US)

(73) Assignee: The Kenneth S. Warren Institute, Inc., Ossining, NY (US)

( * ) Notice: Subject to any disclaimer, the term of this patent is extended or adjusted under 35 U.S.C. 154(b) by 0 days.

(21) Appl. No.: 09/753,132

(22) Filed: Dec. 29, 2000

(65) Prior Publication Data

US 2002/0086816 A1 Jul. 4, 2002

(51) Int. Cl.[7] .............................................. A61K 38/19
(52) U.S. Cl. ...................... 424/85.1; 514/12; 514/912; 530/351; 435/335
(58) Field of Search .......................... 424/85.1; 514/12, 514/912; 530/351; 435/335

(56) References Cited

U.S. PATENT DOCUMENTS

| | | | |
|---|---|---|---|
| 4,377,513 A | 3/1983 | Sugimoto et al. | 530/395 |
| 4,703,008 A | 10/1987 | Lin | 435/240.2 |
| 4,806,524 A | 2/1989 | Kawaguchi et al. | 514/8 |
| 4,835,260 A | 5/1989 | Shoemaker | 530/397 |
| 5,457,089 A | 10/1995 | Fibi et al. | 514/8 |
| 5,547,933 A | 8/1996 | Lin | 514/8 |
| 5,571,787 A | 11/1996 | O'Brien et al. | 514/12 |
| 5,614,184 A | 3/1997 | Sytkowski et al. | 536/23.5 |
| 5,618,698 A | 4/1997 | Lin | 435/69.4 |
| 5,621,080 A | 4/1997 | Lin | 530/380 |
| 5,661,125 A | 8/1997 | Strickland | 514/8 |
| 5,696,080 A | 12/1997 | O'Brien | 514/2 |
| 5,700,909 A | 12/1997 | O'Brien | 530/326 |
| 5,714,459 A | 2/1998 | O'Brien | 514/2 |
| 5,756,349 A | 5/1998 | Lin | 435/325 |
| 5,767,078 A | 6/1998 | Johnson et al. | 514/12 |
| 5,773,569 A | 6/1998 | Wrighton et al. | 530/300 |
| 5,830,851 A | 11/1998 | Wrighton et al. | 514/2 |
| 5,835,382 A | 11/1998 | Wilson et al. | 364/496 |
| 5,856,298 A | 1/1999 | Strickland | 514/8 |
| 5,888,772 A | 3/1999 | Okasinski et al. | 435/69.5 |
| 5,955,422 A | 9/1999 | Lin | 514/8 |
| 6,165,783 A | 12/2000 | Weiss et al. | 435/325 |

FOREIGN PATENT DOCUMENTS

| | | |
|---|---|---|
| WO | WO 95/05465 | 2/1995 |
| WO | WO 97/18318 | 5/1997 |
| WO | WO 97/32895 | 12/1997 |
| WO | WO 98/18926 | 5/1998 |
| WO | WO 00/35475 | 6/2000 |
| WO | WO 01/82952 | 11/2001 |

OTHER PUBLICATIONS

Imai et al. European Journal of Biochemistry, vol.194, No.2, pp. 457–462, 1992.*
Weiland et al. Blut, vol.44, No.3, pp. 173–175, 1982.*
Alafaci et al. European Journal of Pharmacology, vol.406, pp. 219–225, Oct., 2000.*
Anagnostou et al., 1994, "Erythropoietin receptor mRNA expression in human endothelial cells", Proc. Natl. Acad. Sci. USA 91:3974–3978.
Benyo and Conrad, 1999, "Expression of erythropoietin receptor by trophoblast cells in the human placenta", Biol. Reproduct. 60:861–870.
Bernaudin et al., 2000, Neurons and astrocytes express EPO nRNA: oxygen–sensing mechanisms that involve the redox–state of the brain, Glia 30:271–278.
Ehrenreich et al., 2002, "Erythropoietin therapy for acute stroke is both safe and beneficial", Molec. Med., in press.
Farrell et al., 2001, "Erythropoietin crosses the blood brain barrier", Blood 98:148b (abstr. #4265; 43rd Annual Meeting of the American Society of Hematology, Orlando FL, Dec. 7–11, 2001).
Gorio et al., 2002, "Recombinant human erythropoietin counteracts secondary injury and markedly enhances neurological recovery from experimental spinal cord trauma", Proc. Natl. Acad. Sci. USA 99:9450–9455.
Grasso et al., 2002, "Beneficial effects of systemic administration of recombinant human erythrpoiethin in rabbits subjected to subarachnoid hemorrhage", Proc. Natl. Acad. Sci. USA 99:5627–5631.
Gregory et al., 1999, "GATA–1 and erythropoietin cooperate to promote erythroid cell survival by regulating bcl–$x_L$ expression", Blood 94:87–96.
Junk et al., 2002, "Erythropoietin administration protects retinal neurons from acute ischemia–reperfusion injury", Proc. Natl. Acad. Sci. USA 99:10659–10664 (PNAS Early Edition.
Juul et al., 2001, "Recombinant erythropoietin (EPO) crosses the blood brain barrier (BBB) in preterm fetal sheep", Soc. for Neuroscience Abstracts 27:929 (31st Annual Meeting of the Society for Neuroscience, San Diego, CA Nov. 10–15, 2001).
Juul et al., 1998, "Tissue distribution of erythropoietin and erythropoietin receptor in the developing human fetus", Early Human Devel. 52:235–249.
Li et al., 1996, "Erythropoietin receptors are expressed in the central nervous system of mid–trimester human fetuses", Pediatr. Res. 40:376–380.

(List continued on next page.)

*Primary Examiner*—Elizabeth Kemmerer
*Assistant Examiner*—Fozia Hamud
(74) *Attorney, Agent, or Firm*—Pennie & Edmonds LLP

(57) ABSTRACT

Methods and compositions are provided for protecting or enhancing erythropoietin-responsive cell, tissue, organ and bodily part function and viability in vivo, in situ or ex vivo in mammals including human beings by systemic or local administration of an erythropoietin receptor activity modulator, such as an erythropoietin:

16 Claims, 7 Drawing Sheets

OTHER PUBLICATIONS

Liu et al., 1996, "Transgenic mice containing the human erythropoietin receptor gene exhibit correct hematopoietic and neural expression", Proc. Assoc. Am. Physicians 108:449–454.

Mioni et al., 1992, "Evidence for specific binding and stimulatory effects of recombinant human erythropoietin on isolated adult rat Leydig cells", Acta Endocrinologica 127:459–465.

Okada et al., 1996, "Erythropoietin stimulates proliferation of rat–cultured gastric mucosal cells", Digestion 57:328–332.

Sawyer et al., 1989, "Receptors for erythropoietin in mouse and human erythroid cells and placenta", Blood 74:103–109.

Silva et al., 1999, "Erythropoietin can induce the express of bcl-$x_L$ through Stat5 in erythropoietin–dependent proge cell lines", J. Biol. Chem. 274:22165–22169.

Sirén et al., 2001, "Erythropoietin prevents neuronal apoptosis after cerebral ischemia and metabolic stress", Proc. Natl. Acad. Sci. USA 98:4044–4049.

Westenfelder et al., 1999, "Human, rat and mouse kidney cells express functional erythropoietin receptors", Kidney Intl. 55:808–820.

Williams et al., 1994, "Human erythropoietin receptor", Ann. NY Acad. Sci. 718:232–244.

Bernaudin et al., 1999, "A potential role for erythropoietin in focal permanent cerebral ischemia in mice", J. Cereb. Blood Flow Metab. 19:643–651.

Bondy, 1995, "The relaxation of oxidative stress and hyperexcitation to neurological disease", Proc. Soc. Exp. Biol. Med. 208:337–345.

Brines et al., 2000, "Erythropoietin crosses the blood–brain barrier to –protect against experimental brain injury", Proc. Natl. Acad. Sci. USA 97:10526–10531.

Campana et al., 1998, "Identification of a neurotrophic sequence in erythropoietin", Int. J. Mol. Med. 1:235–241.

Digicaylioglu et al. 1995, "Localization of specific erythropoietin binding sites in defined areas of the mouse brain.", Proc. Natl. Acad. Sci. USA 92:3717–3720.

Dipaolo et al., 1992, "Effects of uremia and dialysis on brain electrophysiology after recombinant erythropoietin treatment", ASAIO J. 38:M477–M480.

Grimm et al., 1990, "Improvement of brain function in hemodialysis patients treated with erythropoietin", Kidney Intl. 38:480–486.

Hefti, 1997, "Pharmacology of neurotrophic factors", Annu. Rev. Pharmacol. Toxicol. 37:239–267.

Hengemihle et al., 1996, "Chronic treatment with human recombinant erythropoietin increases hematocrit and improves water maze performance in mice", Physiol. Behav. 59:153–156.

Hirakata et al., 1992, "CBF and oxygen metabolism in hemodialysis patients: effects of anemia correction with recombinant human EPO", Am. J. Physiol. 262:F737–F743.

Juul et al., 1998, "Erythropoietin and erythropoietin receptor in the developing human central nervous system", Pediatr. Res. 43:40–49.

Konishi et al., 1993, "Trophic effect of erythropoietin and other hematopoietic factors on central cholinergic neurons in vitro and in vivo", Brain Res. 609:29–35.

Kopf et al., 1994, "Memory–improving actions of glucose: involvement of a central cholinergic muscarinic mechanism.", Behav. Neural Biol. 62:237–243.

Latini et al., 1998, "Comparative efficacy of a DA2/α2 agonist and a β–blocker in reducing adrenergic drive and cardiac fibrosis in an experimental model of left ventricular dysfunction after coronary artery occlusion", J. Cardiovasc. Pharmacol. 31:601–608.

Li et al., 1998, "A single pre–training glucose injection induces memory facilitation in rodents performing various tasks: contribution of acidic fibroblast growth factor", Neurosci. 85:785–794.

Lipinski et al., 1995, "Nerve growth factor facilitates conditioned taste aversion learning in normal rats", Brain Res. 692:143–153.

Liu et al., 1997, "Regulated human erythropoietin receptor expression in mouse brain", J. Biol. Chem. 272:32395–32400.

Liu et al., 1994, "Tissue specific expression of human erythropoietin receptor in transgenic mice", Devel. Biol. 166:159–169.

Marrero et al., 1998, "Erythropoietin receptor–operated $Ca^{2+}$ channels: activation by phospholipase C–γ1", Kidney Intl. 53:1259–1268.

Marsh et al., 1991, "rHuEPO treatment improves brain and cognitive function of anemic dialysis patients", Kidney Intl. 39:15–163.

Marti et al., 1997, "Detection of erythropoietin in human liquor: intrinsic erythropoietin production in the brain", Kidney Intl. 51:416–418.

Marti et al., 1996, "Erythropoietin gene expression in human, monkey and murine brain", Eur. J. Neurosci. 8:666–676.

Masuda et al., 1997, "Insulin–like growth factors and insulin stimulate erythropoietin production in primary cultured astrocytes", Brain Res. 746:63–70.

Masuda et al., 1994, "A novel site of erythropoietin production. Oxygen–dependent production in cultured rat astrocytes", J. Biol. Chem. 269:19488–19493.

Masuda et al., 1993, "Functional erythropoietin receptor of the cells with neural characteristics. Comparison with receptor properties of erythroid cells", J. Biol. Chem. 268:11208–11216.

Morishita et al., 1997, "Erythropoietin receptor is expressed in rat hippocampal and cerebral cortical neurons, and erythropoietin prevents in vitro glutamate–induced neuronal death", Neurosci. 76:105–116.

Moss and Scholey, 1996, "Oxygen administration enhances memory formation in healthy young adults", Psychopharmacol. 124:255–260.

Nakamura et al., 1998, "Elevated levels of erythropoietin in cerebrospinal fluid of depressed patients", Am. J. Med. Sci. 315:199–201.

Nissenson et al., 1991, "Recombinant human erythropoietin and renal anemia: molecular biology, clinical efficacy and nervous system effects", Ann. Int. Med. 114:402–416.

Nissenson, 1989, "Recombinant human erythropoietin: impact on brain and cognitive function, exercise tolerance, sexual potency and quality of life", Sem. Nephrol. 9(suppl. 2):25–31.

Ogden, 1989, "Monitoring considerations in recombinant human erythropoietin therapy", Sem. Nephrol. 9(suppl. 2):12–15.

Pardridge, 1997, "Drug delivery to the brain", J. Cerebral Blood Flow Metab. 17:713–731.

Pardridge et al., 1991, "Selective transport of an anti–transferrin receptor antibody through the blood–brain barrier in vivo", J. Pharmacol. Exp. Ther. 27:66–70.

Poduslo et al., 1994, "Macromolecular premeability across the blood–nerve and blood–brain barriers", Proc. Natl. Acad. Sci. USA 91:5705–5709.

Prendergast et al., 1997, "Nitric oxide synthase inhibition impairs spatial navigation learning and induces conditioned taste aversion", Pharmacol. Biochem. Behav. 57:347–352.

Rose and Audus, 1998, "Receptor–mediated angiotensin II transcytosis by brain microvessel endothelial cells", Peptides 19:1023–1030.

Sadamoto et al., 1998, "Erythropoietin prevents place navigation disability and cortical infarction in rats with permanent occlusion of the middle cerebral artery", Biochem. Biophys. Res. Comm. 253:26–32.

Sakanaka et al., 1998, "In vivo evidence that erythropoietin protects neurons from ischemic damage", Proc. Natl. Acad. Sci. USA 95:4635–4640.

Tabira et al., 1995, "Neurotrophic effect of hematopoietic cytokines on cholinergic and other neurons in vitro", Int. J. Devl. Neurosci. 13:241–252.

Wolcott et al., 1989, "Recombinant human erythropoietin treatment may improve quality of life and cognitive function in chronic hemodialysis patients", Am. J. Kidney Dis. 14:478–485.

Wu and Pardridge, 1999, "Neuroprotective with noninvasive neurotrophin delivery to the brain", Neurobiol. 96:254–259.

Yamaji et al., 1996, "Brain capillary endothelial cells express two forms of erythropoietin receptor mRNA", Eur. J. Biochem. 239:494–500.

Alafaci et al., 2000, "Effect of Recombinant Human Erythropoietin on Cerebral Ischemia Following Experimental Subarachnoid Hemorrhage," Eur. J. Phar., 406:219–225.

Annable et al., 1972, "The Second International Reference Preparation of Erythropoietin, Human, Urinary, for Bioassay," Bull. Org. mond. Sante, 47:99–112.

Ashwell et al., 1978, "A Protein from Mammalian Liver that Specifically Binds Galactose–Terminated Glycoproteins," Meth. Enzymol., 50:287–291.

Bauer, 1995, "The Oxygen Sensor That Controls EPO Production: Facts and Fancies," J. Perinat. Med., 23:7–12.

Briggs et al., 1974, "Hepatic Clearance of Intact and Desialylated Erythropoietin," Am. J. Physiol., 227:1385–1388.

Bruneval et al., 1993, "Erythropoietin Synthesis by Tumor Cells in a Case of Meningioma Associated With Erythrocytosis," Blood, 81:1593–1597.

Camiscoli et al., 1968, "Comparative Assay of Erythropoietin Standards," Annals New York Acad. Sci., 149:40–45.

Claus–Walker and Dunn, 1984, "Spinal Cord Injury and Serum Erythropoietin," Arch. Phys. Med. Rehabil., 65:370–374.

Cotes, 1968, "Quantitative Estimation of Erythropoietin," Part I. Assay and Standardization of Erythropoietin, Annals New York Acad. Sci., 149:12–17.

Cotes and Bangham, 1961, "Bio–Assay of Erythropoietin in Mice Made Polycythaemic By Exposure to Air at a Reduced Pressure," Nature, 191:1065–1067.

Cotes and Bangham, 1966, "The International Reference Preparation of Erythropoietin," Bull. Org. mond. Sante, 35:751–760.

Dordal et al., 1985, "The Role of Carbohydrate in Erythropoietin Action," Endocrinol., 116:2293–2299.

Dube et al, 1988, "Glycosylation at Specific Sites of Erythropoietin is Essential for Biosynthesis, Secretion, and Biological Function," J. Biol. Chem., 263:17516–17521.

Eur. Pharmacopoeia, 1997, p. 5.

Eur. Pharmacopoeia, Suppl. 2001, pp. 777–782.

Fukuda et al., 1989, "Survival of Recombinant Erythropoietin in the Circulation: The Role of Carbohydrates," Blood, 73:84–89.

Garthoff, 1995, "Safety and Efficacy Testing of Hormones and Related Products," The Report and Recommendations of ECVAM Workshop 9, A.T.L.A., 23:699–711.

Goldwasser et al., 1974, "On the Mechanism of Erythropoietin–Induced Differentiation," XIII. The Role of Sialic Acid in Erythropoietin Action, J. Biol. Chem., 249:4202–4206.

Goldwasser et al., 1975, "An Assay for Erythropoietin in Vitro at the Milliunit Level," Endo., 97:315–323.

Goldwasser and Gross, "Erythropoietin: Assay and Study of Its Mode of Action," Hormone Assays, pp. 109–121.

Hammond et al., 1968, "Production, Utilization and Excretion of Erythropoietin: I. Chronic Anemias. II. Aplastic Crisis. III. Erythropoietic Effects of Normal Plasma," Erythropoietin, 149:516–527.

Horton et al., 1991, "Von Hippel–Lindau Disease and Erythrocytosis: Radioimmunoassay of Erythropoietin in Cyst Fluid From a Brainstem Hemangioblastoma," Neurology, 41:753–754.

Imai et al., 1990, "Physicochemical and Biological Characterization of Asialoerythropoietin," Eur. J. Biochem., 194:457–462.

Keighley, 1968, "Further Experiences with Assays, Units, and Standards of Erythropoietin," Annals New York Acad. Sci., 149:18–24.

Kohama et al., 2000, "Large Uterine Myoma with Erythropoietin Messenger RNA and Erythrocytosis," Obstetrics and Gynecology, 96:826–828.

Lowy et al., 1960, "Inactivation of Erythropoietin by Neuraminidase and by Mild Substitution Reactions," Nature, 185:102–103.

Matsuyama et al., 2000, "Erythrocytosis Caused by an Erythropoietin–Producing Hepatocellular Carcinoma," J. Surg. Oncology, 75:197–202.

Miyake et al., 1977, "Purification of Human Erythropoietin," J. Biol. Chem., 252:5558–5564.

Morrell et al., 1968, "Physical and Chemical Studies on Ceruloplasmin," Metabolic Studies on Sialic Acid–Free Ceruloplasmin In Vivo, J. Biol. Chem., 243:155–159.

Nakamura et al., 1998, "Elevated Levels of Erythropoietin in Cerebrospinal Fluid of Depressed Patients," Am. J. Med. Sci., 315:199–201.

Shiramizu et al., 1994, "Constitutive Secretion of Erythropoietin by Human Renal Adenocarcinoma Cells in Vivo and in Vitro," Exp. Cell Res., 215:249–256.

Shore et al., 1968, "Quantitative Estimation of Erythropoietin," Annals New York Acad. Sci., 149:46–48.

Spivak and Hogans, 1989, "The In Vivo Metabolism of Recombinant Human Erythropoietin in the Rat," Blood, 73:90–99.

Storring et al., 1998, "Epoietin Alfa and Beta Differ In Erythropoietin Isoform Compositions and Biological Properties," British J. Haematology, 100:79–89.

Storring and Gaines Das, 1992, "The International Standard for Recombinant DNA–Derived Erythropoietin: Collaborative Study of Four Recombinant DNA–derived Erythropoietins and Two Highly Purified Human Urinary Erythropoietins," J. Endocrinol., 134:459–484.

Suzuki et al., 2001, "Erythropoietin Synthesis by Tumour Tissues in a Patient With Uterine Myoma and ERythrocytosis," British J. Haematology, 113:49–51.

Weiland et al., "In vivo Activity of Asialo–Erythropoietin in Combination with Asialo–Glycoproteins," 1982, Blut, 44:173–175.

* cited by examiner

PROTECTION AND ENHANCEMENT OF ERYTHROPOIETIN-RESPONSIVE CELLS, TISSUES AND ORGANS

FIELD OF THE INVENTION

The present invention is directed to the protection and enhancement of cells, tissues and organs of a mammalian body that may be isolated or separated from the vasculature by an endothelial cell barrier. Protection is provided to cells, tissues and organs in situ as well as those that may be temporarily removed, for instance, for transplant. Protection and enhancement is offered to cells, tissues and organs that are erythropoietin responsive or those that depend on erythropoietin-responsive cells for at least an aspect of function or viability.

BACKGROUND OF THE INVENTION

For many years, the only clear physiological role of erythropoietin (EPO) had been its control of the production of red blood cells. Recently, several lines of evidence suggest that EPO, as a member of the cytokine superfamily, performs other important physiologic functions which are mediated through interaction with the erythropoietin receptor (EPO-R). These actions include mitogenesis, modulation of calcium influx into smooth muscle cells and neural cells, and effects on intermediary metabolism. It is believed that EPO provides compensatory responses that serve to improve hypoxic cellular microenvironments. Although studies have established that EPO injected intracranially protects neurons against hypoxic neuronal injury, intracranial administration is an impractical and unacceptable route of administration for therapeutic use, particularly for normal individuals. Furthermore, previous studies of anemic patients given EPO have concluded that peripherally-administered EPO is not transported into the brain (Marti et al., 1997, Kidney Int. 51:416-8). Copending U.S. application Ser. No. 09/547,220, the entire contents of which is incorporated herein by reference in its entirety, describes the heretofore unrecognized and unappreciated property that a peripherally-administered erythropoietin is capable of crossing an endothelial cell barrier (e.g., the blood-brain barrier) and providing protection and enhancement of excitable tissue across that barrier, for example, for protection or enhancement of neuronal function. It also describes the use of an erythropoietin as a carrier molecule to facilitate the penetration across an endothelial cell barrier, such as the blood-brain barrier, to serve as a carrier for compounds which alone normally cannot cross such barriers.

It is towards the use of an erythropoietin for protecting or enhancing erythropoietin-responsive cells and associated cells, tissues and organs in situ and ex vivo, as well as delivery of an erythropoietin across an endothelial cell barrier for the purpose of protecting and enhancing erythropoietin-responsive cells and associated cells, tissues and organs distal to the vasculature, that the present invention is directed.

Citation or discussion of a reference herein shall not be construed as an admission that such is prior art to the present invention.

BRIEF SUMMARY OF THE INVENTION

In its broadest aspect, the present invention is directed to compositions and methods for protecting, maintaining or enhancing the function or viability of an erythropoietin-responsive mammalian cell and associated cells, tissues and organs, using compounds which may or may not have erythropoietic activity.

In one aspect, the invention is directed to protecting, maintaining or enhancing the viability of an erythropoietin-responsive mammalian cell, and associated cells, tissues and organs, wherein the mammalian cell, tissue or organ is distal to the vasculature by virtue of a tight endothelial cell barrier. The method involves administering to the vasculature an amount of an erythropoietin which is capable of translocation across the intact endothelial cell barrier and providing benefits to erythropoietin-responsive cells and to associated cells, tissues and organs dependent thereon distal to the vasculature.

The invention is based, in part, on the Applicant's discovery that particularly for chronic treatment for the various purposes herein, it is desirable to utilize an erythropoietin with positive effects on erythropoietin-responsive cells and tissues but lacking erythropoietic activity, to prevent an undesirable rise in hemoglobin concentrations and hematocrit over the course of therapy. Such non-erythropoietic forms of EPO may exhibit lack of stimulating erythropoiesis by any of several non-limiting reasons, such as altered pharmacokinetics or altered activity. For example, a suitable non-erythropoietic form of erythropoietin may have too short of a half-life in circulation to be present at a concentration adequate to recruit proerythroblasts via the erythropoietin receptor. Alternatively, a chemically-modified, mutant, or otherwise altered form of erythropoietin which is not recognized by the erythropoietin receptor on proerythroblasts but maintains or has improved activity at enhancing viability and other positive effects on erythropoietin-responsive cells is embraced herein. As described herein, in the case wherein the EPO is non-erythropoietic, the range of doses may be as described, or may be lower depending on the potency of the non-erythropoietic molecule. Units of activity may be determined based on equivalent activity against the target cells and tissues described herein, as the Units normally used for EPO relate to erythropoiesis and are irrelevant to non-erythropoietic EPOs.

The invention is also based, in part, on the Applicant's discovery that organs and other bodily parts isolated from a mammalian body, such as those intended for transplant, are benefitted by exposure to an erythropoietin.

Thus, one aspect of the invention is directed to a method for protecting, maintaining or enhancing the viability or function of a mammalian cell, tissue, organ or bodily part which includes an erythropoietin-responsive cell or tissue, in which the cell, tissue, organ or bodily part is isolated from the mammalian body. The method includes at least exposing the isolated mammalian cell, tissue, organ or bodily part to an amount of an erythropoietin for a duration which is effective to protect, maintain or enhance the aforementioned viability or function. In non-limiting examples, isolated refers to restricting or clamping the vasculature of or to the cell, tissue, organ or bodily part, such as may be performed during surgery; bypassing the vasculature of the cell, tissue, organ or bodily part; removing the cell, tissue, organ or bodily part from the mammalian body, such may be done in advance of xenotransplantation or prior to and during autotransplantation; or traumatic amputation of a cell, tissue, organ or bodily part. Thus, this aspect of the invention pertains both to the perfusion with an erythropoietin in situ and ex vivo. Ex vivo, the erythropoietin may be provided in a cell, tissue or organ preservation solution. For either aspect, the exposing may be by way of continuous perfusion, pulsatile perfusion, infusion, bathing, injection, or catheterization.

Such adverse conditions to function or viability mentioned above may result from clamping of the vascular supply to an organ during repair or other surgical procedure; isolating a viscus or limb during perfusion to provide high levels of, for example, a chemotherapeutic agent; bypass surgery; transcutaneous procedures in which blood flow to a particular tissue or organ may be temporally compromised, such as endarterectomy, angioplasty, stent placement, and cardiac catheterization. Need for protection of cells and tissues also occurs after traumatic amputation or severance of a bodily part such as a finger, toe or limb, such that may be applied to the severed part during the period before reattachment is performed. Administration of the pharmaceutical composition for the beneficial purposes described herein may be provided prior to the period of time during which the adverse conditions prevail, during the period of time, after the period of time, or any combination of times.

An erythropoietin useful for the practice of the invention includes human or another mammalian erythropoietin, an erythropoietin analog, an erythropoietin mimetic, an erythropoietin fragment, a hybrid erythropoietin molecule, an erythropoietin receptor-binding molecule, an erythropoietin agonist, a renal erythropoietin, a brain erythropoietin, an oligomer of any of the foregoing, a multimer of any of the foregoing, a mutein of any of the foregoing, a congener of any of the foregoing, a naturally-occurring form of any of the foregoing, a synthetic form of any of the foregoing, a recombinant form of any of the foregoing, a glycosylation variant of any of the foregoing, a deglycosylated variant of any of the foregoing, or a combination of any of the foregoing. By way of non-limiting example, the amount of an erythropoietin may be within the range from about 100 picograms/ml to about 1,000 nanograms/ml of erythropoietin, an erythropoietin receptor activity modulator, an erythropoietin-activated receptor modulator, or a combination of any of the foregoing. The amount of erythropoietin also may be about 100 nanograms to about 50 micrograms of an erythropoietin per kilogram of the cell, tissue, organ or bodily part. In terms of vascular concentration, the amount of an erythropoietin may be a dose to achieve about 10 picograms/ml to about 1000 nanograms/ml. However, these amounts are merely illustrative and non-limiting.

In one embodiment, the erythropoietin is non-erythropoietic in vivo, such as but not limited to an asialoerythropoietin, such as human asialoerythropoietin. By way of non-limiting example, the amount of an erythropoietin may be within the range from about 100 picograms/ml to about 1,000 nanograms/ml of erythropoietin, an erythropoietin receptor activity modulator, an erythropoietin-activated receptor modulator, or a combination of any of the foregoing. The amount of a non-erythropoietic erythropoietin also may be about 100 nanograms to about 50 micrograms of an erythropoietin per kilogram of the cell, tissue, organ or bodily part. In terms of vascular concentration, the amount of an erythropoietin may be a dose to achieve about 10 picograms/ml to about 1000 nanograms/ml. However, these doses and amounts are merely illustrative and non-limiting.

The foregoing methods are preferably applicable to human beings, but is useful for any mammal, such as but not limited to companion animals, domesticated animals, livestock and zoo animals.

In another aspect of the invention, a method is provided for protecting, maintaining or enhancing the viability or function of a cell, tissue or organ in a mammal, the cell, tissue or organ including at least an erythropoietin-responsive cell or tissue. The cell, tissue or organ is separated from the vasculature of the mammal by an endothelial cell barrier. The method involves at least administering to the vasculature an amount of an erythropoietin for a duration effective to translocate the erythropoietin across the endothelial cell barrier and to protect, enhance or maintain the viability or function of the cell, tissue or organ. By way of non-limiting examples, the administering of the erythropoietin may be provided by a route such as oral, intravenous, topical, intraluminal, inhalation or parenteral administration, the latter including intravenous, intraarterial, subcutaneous, intramuscular, intraperitoneal, submucosal or intradermal.

By way of non-limiting example, the erythropoietin-responsive cell or tissue may be neuronal, muscle, heart, lung, liver, kidney, small intestine, adrenal cortex, adrenal medulla, capillary endothelial, testes, ovary, or endometrial cells or tissue. These examples of erythropoietin-responsive cells are merely illustrative. In a particular embodiment, the mammalian cell, tissue or organ has expended or will expend a period of time under at least one condition adverse to the viability of the cell, tissue or organ. Such conditions may include traumatic in-situ hypoxia or metabolic dysfunction, surgically-induced in-situ hypoxia or metabolic dysfunction, or in-situ toxin exposure, the latter such as may be associated with chemotherapy or radiation therapy.

An erythropoietin may be dosed to the human being or non-human mammal using an amount, duration and frequency of dosing which achieves the desired enhancement or protection. For chronic administration, it is desirable to avoid increasing the hematocrit by administering an erythropoietin at a dose, duration and frequency of dosing that avoids the erythropoietic activity of the erythropoietin but achieves the desired enhancement as described hereinthroughout. As will be described herein, based on the potency, half-life, and other factors, one of skill in the art may design a dosing regimen which achieves this desired goal.

In the foregoing aspect, the erythropoietin may be human or another mammalian erythropoietin, an erythropoietin analog, an erythropoietin mimetic, an erythropoietin fragment, a hybrid erythropoietin molecule, an erythropoietin receptor-binding molecule, an erythropoietin agonist, a renal erythropoietin, a brain erythropoietin, an oligomer of any of the foregoing, a multimer of any of the foregoing, a mutein of any of the foregoing, a congener of any of the foregoing, a naturally-occurring form of any of the foregoing, a synthetic form of any of the foregoing, a recombinant form of any of the foregoing, a glycosylation variant of any of the foregoing, a deglycosylated variant of any of the foregoing, or a combination of any of the foregoing. In this aspect of the invention, the amount of an erythropoietin may be within the range from about 100 nanograms per kilogram to about 50 micrograms per kilogram of erythropoietin, an erythropoietin receptor activity modulator, an erythropoietin-activated receptor modulator, or a combination thereof, and a pharmaceutically acceptable carrier. A preferred amount of an erythropoietic erythropoietin is about 20 micrograms per kilogram to about 50 micrograms per kilogram. The amount of erythropoietin may also be a dose effective amount to achieve a circulating level of erythropoietin of greater than about 0.5 nanograms/ml to about 1000 nanograms/ml of serum. In a preferred embodiment, the erythropoietin is non-erythropoietic, such as but not limited to an asialoerythropoietin, such as human asialoerythropoietin. In the case of the non-erythropoietic erythropoietin, a preferred amount is 100 nanograms per kilogram up to about 50 micrograms per kilogram; in serum or solution, a concentration of about 10 picograms per milliliter to about 1000 nanograms per milliliter is desirable. Such doses and amounts are merely illustrative and are not intended to be limiting.

In one embodiment, an erythropoietin may have a biological half-life less than 50% that of native human erythropoietin, preferably less than 90% that of native human erythropoietin. As mentioned above, the dose, dosing frequency and duration may be adjusted, particularly for chronic administration, to expose the human being or non-human mammal to an erythropoietin which achieves the desired enhancement or protection but does not induce erythropoiesis or increase hematocrit. Thus, both erythropoietic and non-erythropoietic erythropoietins may be dosed to achieve these desired results. Preferably, for chronic administration, a non-erythropoietic erythropoietin is used. Dosing parameters may also be adjusted for the potency of the particular form of erythropoietin, and particularly a non-erythropoietic form of erythropoietin, for the uses herein.

The foregoing methods are preferably applicable to human beings, but is useful for any mammal, such as but not limited to companion animals, domesticated animals, livestock and zoo animals.

The invention is also directed to a pharmaceutical composition in dosage unit form adapted for modulation of erythropoietin-responsive cells, tissues or organs which includes at least, per dosage unit, an effective non-toxic amount within the range from about 1.5 mg to about 5 mg of an erythropoietin, an erythropoietin receptor activity modulator, an erythropoietin-activated receptor modulator, or a combination of any of the foregoing, and a pharmaceutically acceptable carrier. In one embodiment, the effective non-toxic amount of EPO in the pharmaceutical composition comprises 1 to 5 mg of EPO; 1.5 to 5 mg of EPO; 2 to 5 mg of EPO; 2.5 to 5 mg of EPO; 3.5 to 5 mg of EPO; 4 mg to 5 mg of EPO; or 4.5 to 5 mg of EPO. The erythropoietin may be human or other mammalian erythropoietin, an erythropoietin analog, an erythropoietin mimetic, an erythropoietin fragment, a hybrid erythropoietin molecule, an erythropoietin receptor-binding molecule, an erythropoietin agonist, a renal erythropoietin, a brain erythropoietin, an oligomer of any of the foregoing, a multimer of any of the foregoing, a mutein of any of the foregoing, a congener of any of the foregoing, a naturally-occurring form of any of the foregoing, a synthetic form of any of the foregoing, or a recombinant form of any of the foregoing.

In another aspect, the invention is directed to a pharmaceutical composition in dosage unit form adapted for modulation of erythropoietin-responsive cells, tissues or organs which comprises, per dosage unit, an effective non-toxic amount within the range from about 5 micrograms to 5 mg of a non-erythropoietic erythropoietin, a non-erythropoietic erythropoietin receptor activity modulator, a non-erythropoietic erythropoietin-activated receptor modulator, or a combination of any of the foregoing, and a pharmaceutically acceptable carrier. In a one embodiment, the non-erythropoietic erythropoietin has altered pharmacokinetics compared with native, human erythropoietin, such as but not limited to non-erythropoietic glycosylation variants of erythropoietin or non-erythropoietic deglycosylated variants of erythropoietin; one example being asialoerythropoietin. The ranges may include from about 5 micrograms to 5 mg of a non-erythropoietic erythropoietin; 10 micrograms to 5 mg of a non-erythropoietic erythropoietin; 50 micrograms to 5 mg of a non-erythropoietic erythropoietin; 100 micrograms to 5 mg of a non-erythropoietic erythropoietin; 500 micrograms to 5 mg of a non-erythropoietic erythropoietin; 0.5 mg to 5 mg of a non-erythropoietic erythropoietin; 0.6 mg to 5 mg of a non-erythropoietic erythropoietin; 0.7 mg to 5 mg of a non-erythropoietic erythropoietin; 0.8 mg to 5 mg of a non-erythropoietic erythropoietin; 0.9 mg to 5 mg of a non-erythropoietic erythropoietin; 1 mg to 5 mg of a non-erythropoietic erythropoietin; 1.5 to 5 mg of a non-erythropoietic erythropoietin; 2 to 5 mg of a non-erythropoietic erythropoietin; 2.5 to 5 mg of a non-erythropoietic erythropoietin; 3.5 to 5 mg of a non-erythropoietic erythropoietin; 4 mg to 5 mg of a non-erythropoietic erythropoietin; or 4.5 to 5 mg of a non-erythropoietic erythropoietin.

The invention is also directed to a perfusate solution comprising an erythropoietin, such as but not limited to an erythropoietin, an erythropoietin receptor activity modulator, an erythropoietin-activated receptor modulator, or a combination of any of the foregoing, and a pharmaceutically acceptable carrier. The erythropoietin may be human or another mammalian erythropoietin, an erythropoietin analog, an erythropoietin mimetic, an erythropoietin fragment, a hybrid erythropoietin molecule, an erythropoietin receptor-binding molecule, an erythropoietin agonist, a renal erythropoietin, a brain erythropoietin, an oligomer of any of the foregoing, a multimer of any of the foregoing, a mutein of any of the foregoing, a congener of any of the foregoing, a naturally-occurring form of any of the foregoing, a synthetic form of any of the foregoing, or a recombinant form of any of the foregoing. The perfusate may comprise an erythropoietin at a concentration of about 10 picograms per ml to about 1000 nanograms per ml. However, these amounts are merely illustrative and non-limiting.

These and other aspects of the present invention will be better appreciated by reference to the following Figures and Detailed Description.

DETAILED DESCRIPTION OF THE INVENTION

Figure 1:
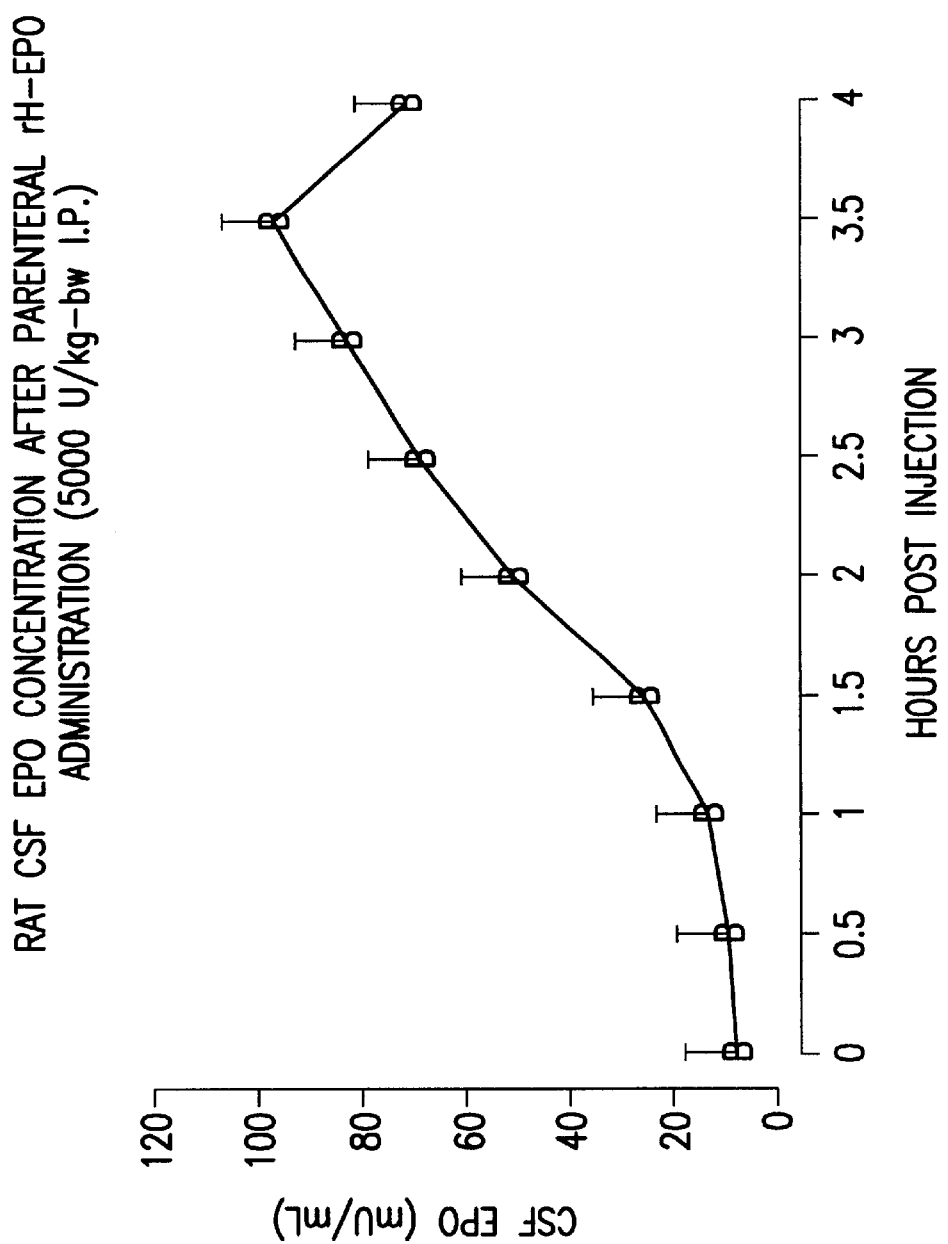
FIG. 1 depicts the translocation of parenterally-administered erythropoietin into the cerebrospinal fluid.

"Erythropoietin-responsive cell" refers to a mammalian cell whose function or viability may be maintained, promoted, enhanced, or in any other way benefitted, by exposure to an erythropoietin. Non-limiting examples of such cells include neuronal, muscle, heart, lung, liver, kidney, small intestine, adrenal cortex, adrenal medulla, capillary endothelial, testes, ovary, and endometrial cells. Moreover, such erythropoietin-responsive cells and the benefits provided thereto by an erythropoietin may be extended to provide protection or enhancement indirectly to other cells that are not directly erythropoietin responsive, or of tissues or organs which contain such non-erythropoietin-responsive cells. These other cells, or tissues or organs which benefit indirectly from the enhancement of erythropoietin-responsive cells present as part of the cells, tissue or organ as "associated" cells, tissues and organs. Thus, benefits of an erythropoietin as described herein may be provided as a result of the presence of a small number or proportion of erythropoietin-responsive cells in a tissue or organ, for example, excitable or neuronal tissue present in such tissue, or the Leydig cells of the testis, which makes testosterone.

The methods of the invention provide for the local or systemic protection or enhancement of cells, tissues and organs within a mammalian body, under a wide variety or normal and adverse conditions, or protection of those which are destined for relocation to another mammalian body. As mentioned above, the ability of an erythropoietin to cross a tight endothelial cell barrier and exert its positive effects on erythropoietin-responsive cells (as well as other types of cells) distal to the vasculature offers the potential to prevent as well as treat a wide variety of conditions and diseases which otherwise wreak significant cellular and tissue damage in an animal, and moreover, permit success of heretofore unattemptable surgical procedures for which risk traditionally outweighed the benefits. The duration and degree of purposeful adverse conditions induced for ultimate benefit, such as high-dose chemotherapy, radiation therapy, prolonged ex-vivo transplant survival, and prolonged periods of surgically-induced ischemia, may be carried out by taking advantage of the invention herein. However, the invention is not so limited, but includes as one aspect, methods or compositions wherein the target erythropoietin-responsive cells are distal to the vasculature by virtue of an endothelial-cell barrier or endothelial tight junctions, but is directed in general to any erythropoietin-responsive cells and associated cells, tissues and organs which may benefit from exposure to an erythropoietin.

The various methods of the invention utilize a pharmaceutical composition which at least includes an erythropoietin at an effective amount for the particular route and duration of exposure to exert positive effects or benefits on erythropoietin-responsive cells within or removed from a mammalian body. Where the target cell, tissues or organs of the intended therapy require the erythropoietin to cross an endothelial cell barrier, the pharmaceutical composition includes the erythropoietin at a concentration which is capable, after crossing the endothelial cell barrier, of exerting its desirable effects upon the erythropoietin-responsive cells. Molecules capable of interacting with the EPO receptor and modulating the activity of the receptor, herein referred to as erythropoietin or erythropoietin receptor activity modulators, are useful in the context of the present invention. These molecules may be, for example, naturally-occurring, synthetic, or recombinant forms of erythropoietin molecules, as described above, or other molecules which may not necessarily resemble erythropoietin in any manner, except to modulate erythropoietin responsive cell activity, as described herein. It also includes chemically-modified forms of any a of the erythropoietin molecules here, such as but not limited to phenylglyoxal-treated erythropoietin or various glycosylation variants of erythropoietin. These molecules may be used in combination for the various purposes herein described.

Erythropoietin is a glycoprotein hormone which in humans has a molecular weight of about 34 kDa. The mature protein comprises 156 amino acids, and the glycosyl residues comprise about 40% of the weight of the molecule. The forms of erythropoietin useful in the practice of the present invention encompass naturally-occurring, synthetic and recombinant forms of the following human and other mammalian erythropoietin-related molecules: erythropoietin, asialoerythropoietin, deglycosylated erythropoietin, erythropoietin analogs, erythropoietin mimetics, erythropoietin fragments, hybrid erythropoietin molecules, erythropoietin receptor-binding molecules, erythropoietin agonists, renal erythropoietin, brain erythropoietin, oligomers and multimers thereof, muteins thereof, and congeners thereof. The term "EPO" and "erythropoietin" as well as "an EPO" or "an erythropoietin" may be used interchangeably or conjunctively, and the various analogs, fragments, hybrid molecules, agonists, muteins, and other forms as described above embrace the variants in the extents of and sites of glycosylation of erythropoietin, including native, deglycosylated, asialylated, and other partially glycosylated forms of erythropoietin. Non-limiting examples of such variants are described in Tsuda et al., 1990, *Eur. J. Biochem.* 188:405–411, incorporated herein by reference. In one embodiment, the erythropoietin used for the purposes herein is non-erythropoietic, such as but not limited to an asialo-erythropoietin. As noted above, the invention herein embraces any and all erythropoietin receptor activity modulator molecules capable of exerting positive activity on erythropoietin-responsive cells, regardless of any structural relationship of the molecule with erythropoietin.

As will be seen in the description herein and the examples below, it is desirable for chronic treatment for the various purposes herein to utilize an erythropoietin with positive effects on erythropoietin-responsive cells and tissues but lacking erythropoietic activity in vivo, to prevent an undesirable rise in hemoglobin concentrations and hematocrit over the course of therapy. Such non-erythropoietic forms of EPO may exhibit lack of stimulating erythropoiesis by any of several non-limiting reasons, for example, having too short of a half-life in circulation to be present at a concentration adequate to recruit proerythroblasts via the erythropoietin receptor. As expression of the erythropoietin receptor on proerythroblasts occurs late in their development, and only for a short period of time, multiple small groups of proerythroblasts become sensitive to EPO sequentially. Unless erythropoietin is present continuously, only a small fraction will be recruited.

As used herein, half-life refers to the biological half-life, or the half-life of the concentration of the intact molecule in plasma or serum. Survival of erythropoietin in circulation is critically dependent on the presence or absence of carbohydrates, especially the terminal sialic acids. For example, the elimination half-life of EPO in the rat is 180 minutes; that of the non-erythropoietic EPO derivative asialoerythropoietin is only two minutes (Spivak and Hogans, 1989, *Blood* 73:90–99). This derivative never reaches circulating concentrations that achieve or support erythropoiesis. In contrast, the erythropoietin receptor is present continuously on other cells such as endothelial, neuronal, and others as described herein, such that a boluses of EPO can maximally saturate the receptors they express and elicit a biological response. By way of illustration and as shown in an example below, two groups of mice were each administered 10 U of EPO subcutaneously such that one group received a single dose (which was rapidly cleared from the circulation) and the other group received a continuous infusion from a delivery device containing a total of 10 U. After three weeks the hemoglobin concentration was found to be unchanged in the first group, whereas a significant increase in hematocrit occurred in the group receiving the continuous infusion of the same amount of EPO.

Thus, as will be seen herein, particularly for chronic administration for the purposes herein, it is desirable to expose a human being or non-human mammal with a dose, duration and/or frequency of administration, by the appropriate route, to achieve the desirable effects herein without inducing erythropoiesis or causing a rise in the hematocrit. The dosing parameters (dose, frequency, duration, route, etc.) will be readily determinable by the skilled artisan based on the potency, biological half-life and other pharmacokinetic parameters of the particular erythropoietin being administered, among other factors. As will be seen herein, a non-erythropoietic erythropoietin may be non-erythropoietic as a result of any one or a combination of factors including but not limited to its structure, extent of sialylation or carbohydrate content, interaction with an erythropoietin receptor, absorption, distribution, clearance and elimination kinetics in the body, susceptibility to degradation, among others. Such factors will be taken into account in providing a dosing regimen including the route, dose, frequency of administration, in order to achieve the desired objects of the invention preferably without increasing the hematocrit.

In addition to the above, other modifications of the erythropoietin molecule to reduce or eliminate erythropoietic activity are embraced by the present invention, such as modification or elimination of portions of the molecule responsible for interaction with the receptor responsible for erythropoiesis, or a peptide or other small molecule without such activity, as will be further elaborated upon below. The means by which the erythropoietic activity of erythropoietin is absent from the preferred embodiment of the invention for the intended uses herein are not intended to be limiting in any way, and the examples described merely illustrative.

In addition to the many known and as yet unknown candidate compounds unrelated to EPO but still interact with and benefit EPO-responsive tissues, EPO itself may be modified to tailor its activities for a specific tissue or tissues. Several non-limiting strategies may be carried out to achieve this desired tissue specificity, include modifications that shorten circulating half-life and thus reducing the time modified EPO can interact with erythroid precursors, or modification of the primary structure of the EPO molecule. One approach to reducing circulating half life is to remove or modify the glycosylation moieties, of which EPO has three N-linked and one O-linked. Such variants of glycosylated EPO can be produced in a number of ways. For example, the sialic acids which terminate the end of the sugar chains can be removed by specific sialidases depending on the chemical linkage connecting the sialic acid to the sugar chain. Alternatively, the glycosylated structure can be dismantled in different ways by using other enzymes that cleave at specific linkages. Techniques to modify the primary structure are myriad and include substitution of specific amino acids, chemical modification of amino acids, or addition of other structures which interfere with the interaction of EPO with any of its receptors. Use of such modified forms of EPO are fully embraced herein. In a preferred embodiment, the half-life of the non-erythropoietic erythropoietin of the invention is reduced by about 90% from that of native erythropoietin.

In addition, a number of mutant EPO molecules have been described which do not bind to the erythrocyte EPO receptor and thus do not support erythropoiesis in vivo or in vitro. Some of these molecules will nevertheless mimic the actions of EPO itself in other tissues or organs. For example, a 17-mer containing the amino-acid sequence of 31–47 of native EPO is inactive for erythropoiesis but fully active for neural cells in vitro (Campana & O'Brien, 1998: Int. J. Mol. Med. 1:235–41). Such non-erythropoietic mutant EPO molecules and peptides are fully embraced herein.

Furthermore, derivative EPO molecules desirable for the uses described herein may be generated by guanidination, amidination, trinitrophenylation, acetylation, succinylation, nitration, or modification of arginine residues or carboxyl groups, among other procedures, to produce erythropoietins which maintain an adequate level of activities for specific organs and tissues but not for others, such as erythrocytes. When erythropoietin is subjected to the above reactions, it has been found that in general the resultant molecule lacks both in-vivo and in-vitro erythropoietic activity (e.g., Satake et al; 1990, Biochim. Biophys. Acta 1038:125–9). One non-limiting example as described hereinbelow is the modification of erythropoietin arginine residues by reaction with phenylglyoxal (according to the protocol of Takahashi, 1977, J. Biochem. 81:395–402). As will be seen below, such a modified EPO molecule fully retains its neurotrophic effect. Such modified erythropoietin molecules are fully embraced for the various uses and compositions described herein.

Synthetic and recombinant molecules, such as brain erythropoietin and renal erythropoietin, recombinant mammalian forms of erythropoietin, as well as its naturally-occurring, tumor-derived, and recombinant isoforms, such as recombinantly-expressed molecules and those prepared by homologous recombination are provided herein. Furthermore, the present invention includes molecules including peptides which bind the erythropoietin receptor, as well as recombinant constructs or other molecules which possess part or all of the structural and/or biological properties of erythropoietin, including fragments and multimers of erythropoietin or its fragments. Erythropoietin herein embraces molecules with altered erythropoietin receptor binding activities, preferably with increased receptor affinity, in particular as pertains to enhancing transport across endothelial cell barriers. It also includes erythropoietin variants that are less or non-erythropoietic. Muteins comprising molecules which have additional or reduced numbers of glycosylation sites are included herein. As noted above, the terms "erythropoietin," "erythropoietin," and "mimetics" as well as the other terms are used interchangeably herein to refer to the erythropoietin-responsive cell protective and enhancing molecules related to erythropoietin as well as the molecules which are capable of crossing endothelial cell barriers. Furthermore, molecules produced by transgenic animals are also encompassed here. It should be noted that erythropoietin molecules as embraced herein do not necessarily resemble erythropoietin structurally or in any other manner, except for ability to interact with the erythropoietin receptor or modulate erythropoietin receptor activity or activate erythropoietin-activated signaling cascades, as described herein.

By way of non-limiting example, forms of erythropoietin useful for the practice of the present invention include erythropoietin muteins, such as those with altered amino acids at the carboxy terminus described in U.S. Pat. No. 5,457,089 and in U.S. Pat. No. 4,835,260; erythropoietin isoforms with various numbers of sialic acid residues per molecule, such as described in U.S. Pat. No. 5,856,292; polypeptides described in U.S. Pat. No. 4,703,008; agonists described in U.S. Pat. No. 5,767,078; peptides which bind to the erythropoietin receptor as described in U.S. Pat. No.

5,773,569 and 5,830,851; small-molecule mimetics which activate the erythropoietin receptor, as described in U.S. Pat. No. 5,835,382; and erythropoietin analogs described in WO 9505465, WO 9718318, and WO 9818926. All of the aforementioned citations are incorporated herein to the extent that such disclosures refer to the various alternate forms or processes for preparing such forms of the erythropoietins of the present invention.

Erythropoietin can be obtained commercially, for example, under the trademarks of PROCRIT, available from Ortho Biotech Inc., Raritan, N.J., and EPOGEN, available from Amgen, Inc., Thousand Oaks, Calif.

The activity (in units) of erythropoietin (EPO) and EPO-like molecules is traditionally defined based on its effectiveness in stimulating red cell production in rodent models (and as derived by international standards of EPO). One unit (U) of regular EPO (MW of ~34,000) is ~10 ng of protein (1 mg protein is approximately 100,000 U). However, as mentioned above, one aspect of, and a preferred embodiment of the invention involves the use of non-erythropoietic forms of erythropoietin or non-erythropoietic EPO-like molecules, such as asialoerythropoietin, and as such, this definition based on erythropoietic activity is inappropriate. Thus, as used herein, the activity unit of EPO or EPO-related molecules is defined as the amount of protein required to elicit the same activity in neural or other erythropoietin-responsive cellular systems as is elicited by native EPO in the same system. Such systems are described herein as well as in Serial Nos. 60/129,131 and 09/547,220, both incorporated herein by reference. The skilled artisan will readily determine the units of a non-erythropoietic erythropoietin or related molecule following the guidance herein.

In the practice of one aspect of the present invention, a pharmaceutical composition as described above containing an erythropoietin may be administered to a mammal by any route which provides a sufficient level of an erythropoietin in the vasculature to permit translocation across an endothelial cell barrier and beneficial effects on erythropoietin-responsive cells. When used for the purpose of perfusing a tissue or organ, similar results are desired. In the instance where the cells or tissue is non-vascularized and/or the administration is by bathing the cells or tissue with the composition of the invention, the pharmaceutical composition provides an effective erythropoietin-responsive-cell-beneficial amount of an erythropoietin. The endothelial cell barriers across which an erythropoietin may translocate include tight junctions, perforated junctions, fenestrated junctions, and any other types of endothelial barriers present in a mammal. A preferred barrier is an endothelial cell tight junction, but the invention is not so limiting.

In one embodiment, the invention provides a pharmaceutical composition in dosage unit form adapted for protection or enhancement of erythropoietin-responsive cells, tissues or organs distal to the vasculature which comprises, per dosage unit, an effective non-toxic amount within the range from about 0.5 mg to 5 mg of EPO; 0.6 mg to 5 mg of EPO; 0.7 mg to 5 mg of EPO; 0.8 mg to 5 mg of EPO; 0.9 mg to 5 mg of EPO; 1 to 5 mg of EPO; 1.5 to 5 mg of EPO; 2 to 5 mg of EPO; 2.5 to 5 mg of EPO; 3.5 to 5 mg of EPO; 4 mg to 5 mg of EPO; or 4.5 to 5 mg of EPO. of erythropoietin, an erythropoietin receptor activity modulator, or an erythropoietin-activated receptor modulator and a pharmaceutically acceptable carrier. In a preferred embodiment, the effective non-toxic amount of an erythropoietic erythropoietin is within the range from about 2 mg to about 5 mg. In a preferred embodiment, the erythropoietin in the aforementioned composition is non-erythropoietic, at a range of about 5 micrograms to 5 mg of a non-erythropoietic erythropoietin; 10 micrograms to 5 mg of a non-erythropoietic erythropoietin; 50 micrograms to 5 mg of a non-erythropoietic erythropoietin; 100 micrograms to 5 mg of a non-erythropoietic erythropoietin; 500 micrograms to 5 mg of a non-erythropoietic erythropoietin; 0.5 mg to 5 mg of a non-erythropoietic erythropoietin; 0.6 mg to 5 mg of a non-erythropoietic erythropoietin; 0.7 mg to 5 mg of a non-erythropoietic erythropoietin; 0.8 mg to 5 mg of a non-erythropoietic erythropoietin; 0.9 mg to 5 mg of a non-erythropoietic erythropoietin; 1 mg to 5 mg of a non-erythropoietic erythropoietin; 1.5 to 5 mg of a non-erythropoietic erythropoietin; 2 to 5 mg of a non-erythropoietic erythropoietin, 2.5 to 5 mg of a non-erythropoietic erythropoietin; 3.5 to 5 mg of a non-erythropoietic erythropoietin; 4 mg to 5 mg of a non-erythropoietic erythropoietin; or 4.5 to 5 mg of a non-erythropoietic erythropoietin.

In one embodiment, such a pharmaceutical composition of erythropoietin may be administered systemically to protect or enhance the target cells, tissue or organ. Such administration may be parenterally, transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration.

In a preferred embodiment, an erythropoietin may be administered systemically at a dosage between 100 nanograms to about 50 micrograms per kg body weight, preferably about 20 micrograms to about 50 micrograms per kg-body weight. In the instance where an erythropoietic erythropoietin is used, the range may preferably be about 20 micrograms to about 50 micrograms per kg body weight. This effective dose should be sufficient to achieve serum levels of erythropoietin from about 10 picograms to about 1000 nanograms per ml of serum after erythropoietin administration. Such serum levels may be achieved at about 1, 2, 3, 4, 5, 6, 7, 8, 9, or 10 hours post-administration. Such dosages may be repeated as necessary. For example, administration may be repeated daily, or every other, third, fourth, fifth, sixth, or seventh day, as long as clinically necessary, or after an appropriate interval, e.g., every 1 to 12 weeks, preferably, every 3 to 8 weeks. In one embodiment, the effective amount of erythropoietin and a pharmaceutically acceptable carrier may be packaged in a single dose vial or other container. In one embodiment, an erythropoietin is non-erythropoietic, i.e., it is capable of exerting the activities described herein but not causing an increase in hemoglobin concentration or hematocrit. Such a non-erythropoietic form of erythropoietin is preferred in instances wherein the methods of the present invention are intended to be provided chronically. In another embodiment, an erythropoietin is given at a dose greater than that necessary to maximally stimulate erythropoiesis.

For other routes of administration, such as by use of a perfusate, injection into an organ, or other local administration, a pharmaceutical composition will be provided which results in similar levels of an erythropoietin as described above. A level of about 10 pg/ml to about 1000 ng/ml is desired.

The pharmaceutical compositions of the invention may comprise a therapeutically effective la amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of an erythropoietin may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering an erythropoietin to multiple sites in the severed part as soon as practicable, even before the arrival of medical personnel on site, or arrival of the afflicted individual with severed toe in tow at the emergency room.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations preferably contain 10% to 95% active ingredient.

A perfusate composition may be provided for use in transplanted organ baths, for in situ perfusion, or for administration to the vasculature of an organ donor prior to organ harvesting Such pharmaceutical compositions may comprise levels of an erythropoietin or a form of an erythropoietin not suitable for acute or chronic, local or system administration to an individual, but will serve the functions intended herein in a cadaver, organ bath, organ perfusate, or in situ perfusate prior to removing or reducing the levels of the erythropoietin contained therein before exposing or returning the treated organ or tissue to regular circulation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, erythropoietin can be delivered in a controlled-release system. For example, the polypeptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Eng. J. Med. 321:574). In another embodiment, the compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); WO 91/04014; U.S. Pat. No. 4,704,355; Lopez-Berestein, ibid., pp. 317–327; see generally ibid.). In another embodiment, polymeric materials can be used [see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: N.Y. (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105).

In yet another embodiment, a controlled release system can be placed in proximity of the therapeutic target, i.e., the target cells, tissue or organ, thus requiring only a fraction of the systemic dose (see, e.g., Goodson, pp. 115–138 in Medical Applications of Controlled Release, vol. 2, supra, 1984). Other controlled release systems are discussed in the review by Langer (1990, Science 249:1527–1533).

In another embodiment, erythropoietin, as properly formulated, can be administered by nasal, oral, rectal, vaginal, or sublingual administration.

In a specific embodiment, it may be desirable to administer the erythropoietin compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of erythropoietin, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

In another aspect of the invention, a perfusate or perfusion solution is provided for perfusion and storage of organs for transplant, the perfusion solution including an amount of an erythropoietin effective to protect erythropoietin-responsive cells and associated cells, tissues or organs. Transplant includes but is not limited to xenotransplantation, where a organ (including cells, tissue or other bodily part) is harvested from one donor and transplanted into a different recipient; and autotransplant, where the organ is taken from one part of a body and replaced at another, including bench surgical procedures, in which an organ may be removed, and while ex vivo, resected, repaired, or otherwise manipulated, such as for tumor removal, and then returned to the original location. In one embodiment, the perfusion solution is the University of Wisconsin (UW) solution (U.S. Pat. No. 4,798,824) which contains from about 1 to about 25 U/ml erythropoietin, 5% hydroxyethyl starch (having a molecular weight of from about 200,000 to about 300,000 and substantially free of ethylene glycol, ethylene chlorohydrin, sodium chloride and acetone); 25 mM $KH_2PO_4$; 3 mM glutathione; 5 mM adenosine; 10 mM glucose; 10 mM HEPES buffer; 5 mM magnesium gluconate; 1.5 mM $CaCl_2$. 105 mM sodium gluconate; 200,000 units penicillin; 40 units insulin; 16 mg Dexamethasone; 12 mg Phenol Red; and has a pH of 7.4–7.5 and an osmolality of about 320 mOsm/l. The solution is used to maintain cadaveric kidneys and pancreases prior to transplant. Using the solution, preservation may be extended beyond the 30-hour limit recommended for cadaveric kidney preservation. This particular perfusate is merely illustrative of a number of such solutions that may be adapted for the present use by inclusion of an effective amount of an erythropoietin. In a further embodiment, the perfusate solution contains from about 5 to about 35 U/ml erythropoietin, or from about 10 to about 30 U/ml erythropoietin.

While the preferred recipient of an erythropoietin for the purposes hereinthroughout is a human, the methods herein apply equally to other mammals, particularly domesticated animals, livestock, companion and zoo animals. However, the invention is not so limiting and the benefits may be applied to any mammal.

In another aspect of the invention, methods and compositions for enhancing the viability of cells, tissues or organs which are not isolated from the vasculature by an endothelial cell barrier are provided by exposing the cells, tissue or organs directly to a pharmaceutical composition comprising an erythropoietin, or administering or contacting an erythropoietin-containing pharmaceutical composition to the vasculature of the tissue or organ. Enhanced activity of erythropoietin-responsive cells in the treated tissue or organ are responsible for the positive effects exerted.

As described above, the invention is based, in part, on the discovery that erythropoietin molecules can be transported from the luminal surface to the basement membrane surface of endothelial cells of the capillaries of organs with endothelial cell tight junctions, including, for example, the brain, retina, and testis. Thus, erythropoietin-responsive cells across the barrier are susceptible targets for the beneficial effects of erythropoietin, and others cell types or tissues or organs which contain and depend in whole or in part on erythropoietin-responsive cells therein are targets for the methods of the invention. While not wishing to be bound by any particular theory, after transcytosis of erythropoietin, erythropoietin can interact with an erythropoietin receptor on an erythropoietin-responsive cell, for example, neuronal, muscle, heart, lung, liver, kidney, small intestine, adrenal cortex, adrenal medulla, capillary endothelial, testes, ovary, or endometrial cell, and receptor binding can initiate a signal transduction cascade resulting in the activation of a gene expression program within the erythropoietin-responsive cell or tissue, resulting in the protection of the cell or tissue, or organ, from damage, such as by toxins, chemotherapeutic agents, radiation therapy, hypoxia, etc. Thus, methods for protecting erythropoietin-responsive cell-containing tissue from injury or hypoxic stress, and enhancing the function of such tissue are described in detail hereinbelow.

In the practice of one embodiment of the invention, a mammalian patient is undergoing systemic chemotherapy for cancer treatment, including radiation therapy, which commonly has adverse effects such as nerve, lung, heart, ovarian or testicular damage. Administration of a pharmaceutical composition comprising an erythropoietin as described above is performed prior to and during chemotherapy and/or radiation therapy, to protect various tissues and organs from damage by the chemotherapeutic agent, such as to protect the testes. Treatment may be continued until circulating levels of the chemotherapeutic agent have fallen below a level of potential danger to the mammalian body.

In the practice of another embodiment of the invention, various organs were planned to be harvested from a victim of an automobile accident for transplant into a number of recipients, some of which required transport for an extended distance and period of time. Prior to organ harvesting, the victim was infused with a pharmaceutical composition comprising an erythropoietin as described herein. Harvested organs for shipment were perfused with a perfusate containing erythropoietin as described herein, and stored in a bath comprising erythropoietin. Certain organs were continuously perfused with a pulsatile perfusion device, utilizing a perfusate containing an erythropoietin in accordance with the present invention. Minimal deterioration of organ function occurred during the transport and upon implant and reperfusion of the organs in situ.

In another embodiment of the invention, a surgical procedure to repair a heart valve required temporary cardioplegia and arterial occlusion. Prior to surgery, the patient was infused with 500 U erythropoietin per kg body weight. Such treatment prevented hypoxic ischemic cellular damage, particularly after reperfusion.

The present invention may be better understood by reference to the following non-limiting Example, which are provided as exemplary of the invention. The following examples are presented in order to more fully illustrate the preferred embodiments of the invention. They should in no way be construed, however, as limiting the broad scope of the invention.

EXAMPLE 1

EPO Crosses the Blood-cerebrospinal Fluid Tight Barrier

Adult male Sprague-Dawley rats were anesthetized and administered recombinant human erythropoietin intraperitoneally. Cerebrospinal fluid was sampled from the cisterna magna at 30 minute intervals up to 4 hrs and the EPO concentration determined using a sensitive and specific enzyme-linked immunoassay. As illustrated in FIG. 1, the baseline EPO concentration in CSF is 8 mU/ml. After a delay of several hours, the levels of EPO measured in the CSF begin to rise and by 2.5 hours and later are significantly different from the baseline concentration at the $p<0.01$ level. The peak level of about 100 mU/ml is within the range known to exert protective effects in vitro (0.1 to 100 mU/ml). The time to peak occurs at about 3.5 hrs, which is delayed significantly from the peak serum levels (less than 1 hr). The results of this experiment illustrate that significant levels of EPO can be accomplished across a tight cellular junction by bolus parenteral administration of EPO at appropriate concentrations.

EXAMPLE 2

Maintenance of Function in Heart Prepared for Transplantation

Wistar male rats weighing 300 to 330 g are given EPO (5000 UI/kg body weight) or vehicle 24 h prior to removal of the heart for ex vivo studies, done in accordance with the protocol of Delcayre et al., 1992, *Amer. J. Physiol.* 263:H1537–45. Animals are sacrificed with pentobarbital (0.3 mL), and intravenously heparinized (0.2 mL). The hearts are initially allowed to equilibrate for 15 min The left ventricular balloon is then inflated to a volume that gives an end-diastolic pressure of 8 mmHg. A left ventricular pressure-volume curve is constructed by incremental inflation of the balloon volume by 0.02 ml aliquots. Zero volume is defined as the point at which the left ventricular end-diastolic pressure is zero. On completion of the pressure-volume curve, the left ventricular balloon is deflated to set end-diastolic pressure back to 8 mmHg and the control period is pursued for 15 min, after check of coronary flow. Then the heart is arrested with 50 mL Celsior+molecule to rest at 4° C. under a pressure of 60 cm $H_2O$. The heart is then removed and stored 5 hours at 4° C. in plastic container filled with the same solution and surrounded with crushed ice.

On completion of storage, the heart is transferred to a Langendorff apparatus. The balloon catheter is re-inserted into the left ventricle and re-inflated to the same volume as during preischemic period. The heart is re-perfused for at least 2 hours at 37° C. The re-perfusion pressure is set at 50 cm $H_2O$ for 15 min of re-flow and then back to 100 cm $H_2O$ for the 2 next hours. Pacing (320 beats per minute) is re-instituted. Isovolumetric measurements of contractile indexs and diastolic pressure are taken in triplicate at 25, 45, 60, 120 min of reperfusion. At this time point pressure volume curves are performed and coronary effluent during the 45 mn reperfusion collected to measure creatine kinase leakage. The two treatment groups are compared using an unpaired t-test, and a linear regression using the end-diastolic pressure data is used to design compliance curves. A significant improvement of volume-pressure curve, decrease of left diastolic ventricular pressure and decrease of creatine kinase leakage indicate improvement of recovery of cold-stored hearts after treatment with erythropoietin.

EXAMPLE 3

EPO Protects Myocardium from Ischemic Injury

Figure 2:
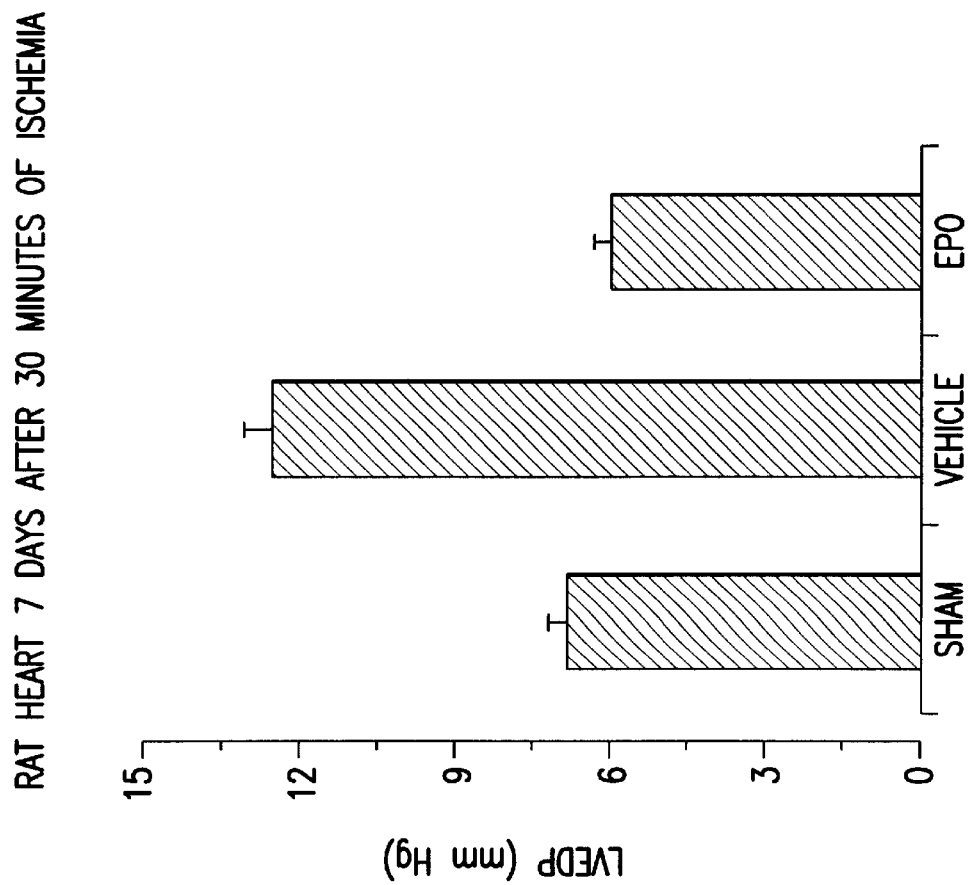
FIG. 2 shows the protection of myocardium to ischemic damage by erythropoietin.
Figure 3:
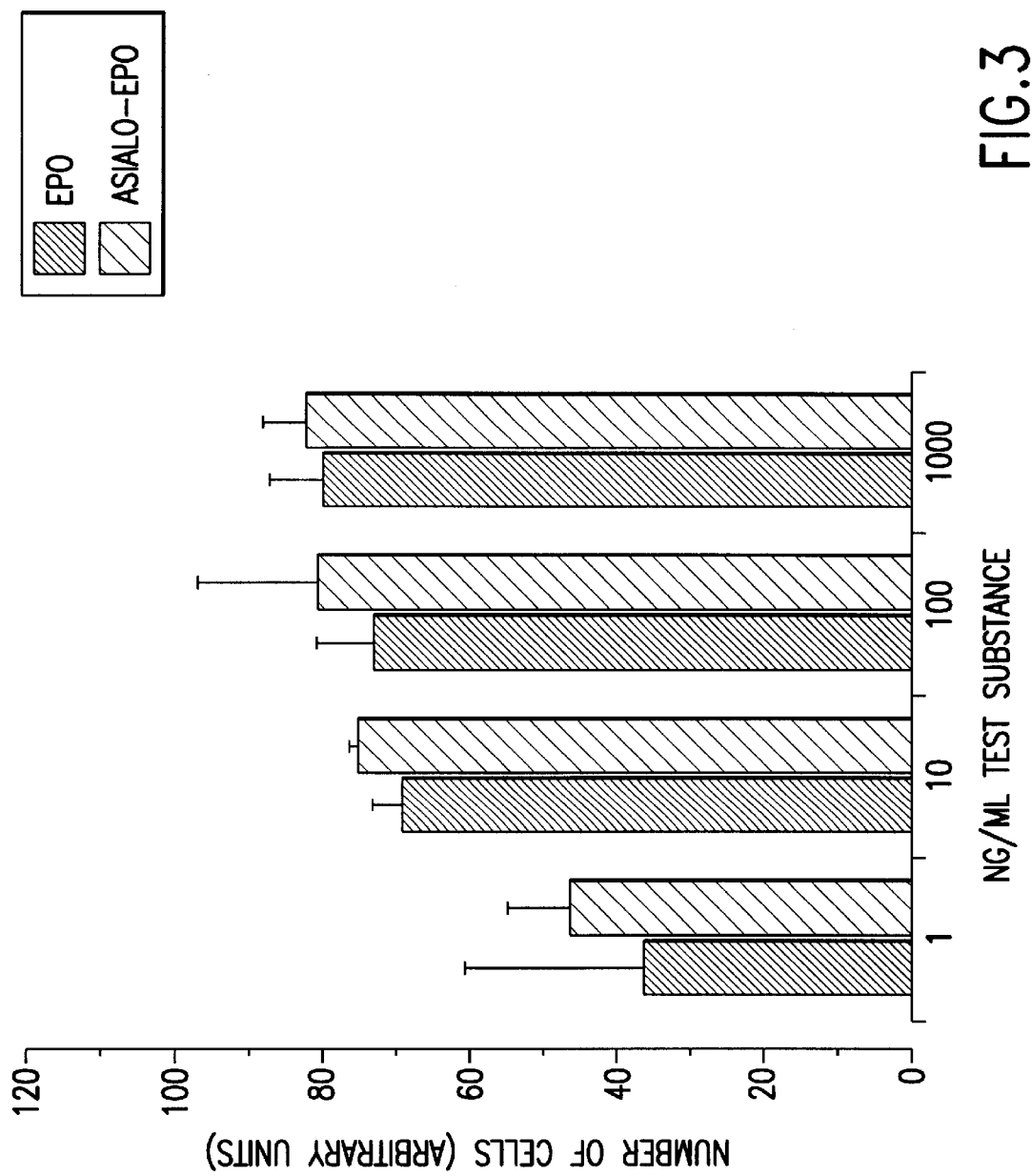
FIG. 3 compares the in-vitro efficacy of erythropoietin and asialoerythropoietin on viability of serum-starved P19 cells.
Figure 4:
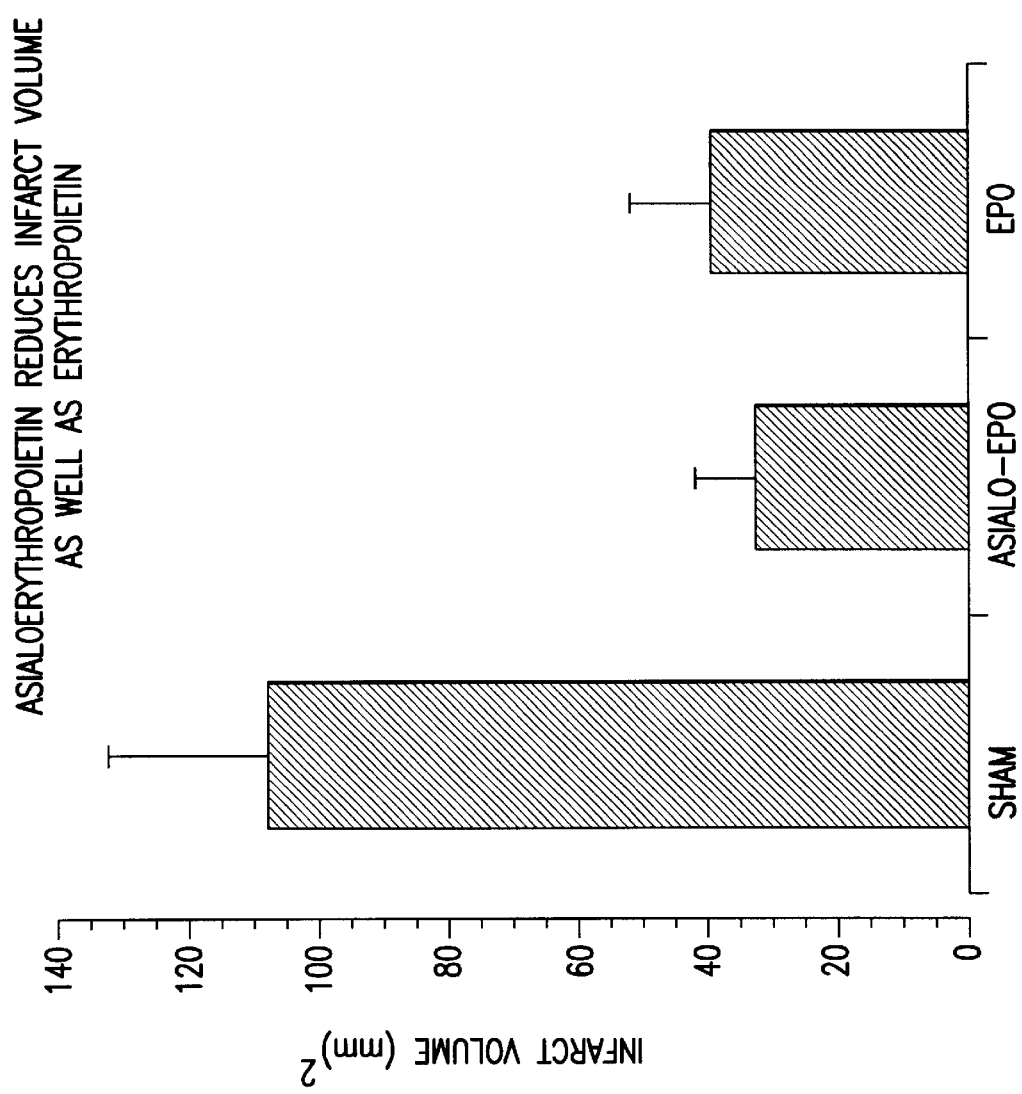
FIG. 4 shows protection of erythropoietin and asialoerythropoietin in a rat focal cerebral ischemia model.

Adult male rats given rhEPO (5000 U/kg body weight) 24 hrs previously are anesthetized and prepared for coronary artery occlusion. An additional dose of EPO is given at the start of the procedure and the left main coronary artery occluded for 30 minutes and then released. The same dose of EPO is given daily for one week after treatment. The animals are then studied for cardiac function. As FIG. 2 illustrates, animals receiving a sham injection (saline) demonstrated a large increase in the left end diastolic pressure, indicative of a dilated, stiff heart secondary to myocardial infarction. In contradistinction, animals receiving EPO suffered no decrement in cardiac function, compared to sham operated controls (difference significant at the $p<0.01$ level).

EXAMPLE 4

Generation of Molecules that Possess Activities in Erythropoietin-responsive Organs or Tissues but are Inactive at Raising the Hemoglobin Concentration in Vivo There are many diseases and conditions that are chronic or subacute in nature and therefore likely require many doses of EPO to confer adequate and prolonged protection in accordance with the methods and uses described herein. If native EPO is used chronically to treat these conditions, in most cases treatment will be accompanied by a gradual, undesirable rise in the hemoglobin level and hematocrit. Evidence illustrating that the biological half life of an EPO-receptor-activating molecule is critical for producing an erythrocytic response was obtained by the following experiment. Two groups of 6 female mice were each administered 10 U of EPO subcutaneously such that group I received a single dose (which was rapidly cleared from the circulation) and group II received a continuous infusion from a delivery device containing a total of 10 U. After three weeks the hemoglobin concentration was determined to be unchanged in group I (12.5 g/dL; SEM 0.25) whereas group II exhibited a significant increase (13.5 g/dL; SEM 0.26; $p<0.01$). Therefore, use of compounds which benefit the tissue or organ targeted for IE protection but do not affect the red cell mass is desired and preferred for uses herein. In addition to the many known and as yet unknown candidate compounds unrelated to EPO but that still interact with and benefit EPO-responsive tissues, EPO itself may be modified to tailor its activities for a specific tissue or tissues. Several non-limiting strategies that may be carried out to achieve this desired tissue specificity include modifications that shorten circulating half-life and thus reducing the time modified EPO can interact with erythroid precursors or modification of the primary structure of the EPO molecule. One approach to reducing circulating half life is to remove or modify the glycosylation moieties, of which EPO has three N-linked and one O-linked. Such variants of glycosylated EPO can be produced in a number of ways. For example, the sialic acids which terminate the end of the sugar chains can be removed by specific sialidases depending on the chemical linkage connecting the sialic acid to the sugar chain. Alternatively, the glycosylated structure can be dismantled in different ways by using other enzymes that cleave at specific linkages. Techniques to modify the primary structure are myriad and include substitution of specific amino acids, chemical modification of amino acids, or addition of other structures which interfere with the interaction of EPO with any of its receptors. Use of such modified forms of EPO are fully embraced herein.

To validate these principles, recombinant human EPO was desialized using Sialidase A (Prozyme Inc) according to the manufacturer's protocol. Successful chemical modification was confirmed by running the reaction product on an SDS polyacrylamide gel and staining the resultant bands which showed that the chemically-modified EPO possessed an apparent molecular weight of ~31 kD as expected, compared to unmodified EPO which was ~34 kD. The asialoerythropoietin or unmodified EPO was then administered intraperitoneally to Balb/c mice at a dose of 10 U every other day for two weeks, and serial hemoglobin concentrations were determined (which showed that no differences between treatment groups occurred). Although administration of the unmodified EPO produced the expected rise in hemoglobin over the two week period ($p<0.05$), administration of asialoEPO did not, consistent with a loss of erythropoietic activity. However, asialoEPO was as effective as native EPO for neural cells in vitro and in vivo as shown in FIGS. 3 and 4. In-vitro testing (FIG. 3) was carried out using neural-like embryonal carcinoma cells (P19) that undergo apoptosis upon the withdrawal of serum. Twenty-four hours before the removal of serum, 1–1000 ng/ml of EPO or asialoEPO were added to the cultures. The following day the medium was removed, the cells washed with fresh, non-serum containing medium, and medium containing the test substance (no serum) added back to the cultures for and additional 48 hours. To determine the number of viable cells, a tetrazolium reduction assay was performed (CellTiter 96; Promega, Inc.). As FIG. 3 illustrates, asialoEPO appears to be of equal potency to EPO itself in preventing cell death.

Retention of neuroprotective activity in vivo was confirmed using a rat focal ischemia model in which a reversible lesion in the territory of the middle cerebral artery is performed as described previously (Brines et al., 2000, *Proc. Nat. Acad. Sci. U.S.A.* 97:10526–31). Adult male Sprague-Dawley rats were administered asialoEPO or EPO (5000 U/kgBW intraperitoneally) or vehicle at the onset of the arterial occlusion. Twenty-four hours later, the animals were sacrificed and their brains removed for study. Serial sections were cut and stained with tetrazolium salts to identify living regions of the brain. As shown in FIG. 4, asialoEPO was as effective as native EPO in providing neuroprotection from 1 hour of ischemia.

EXAMPLE 5

Modification of Primary Structure of EPO and Effectiveness at Neuronal Protection A number of mutant EPO molecules have been described which do not bind to the erythrocyte l EPO receptor and thus do not support erythropoiesis in vivo or in vitro. Some of these molecules will nevertheless mimic the actions of EPO itself in other tissues or organs. For example, a 17-mer containing the amino-acid sequence of 31–47 of native EPO is inactive for erythropoiesis but fully active for neural cells in vitro (Campana & O'Brien, 1998: Int. J. Mol. Med. 1:235–41).

Figure 5:
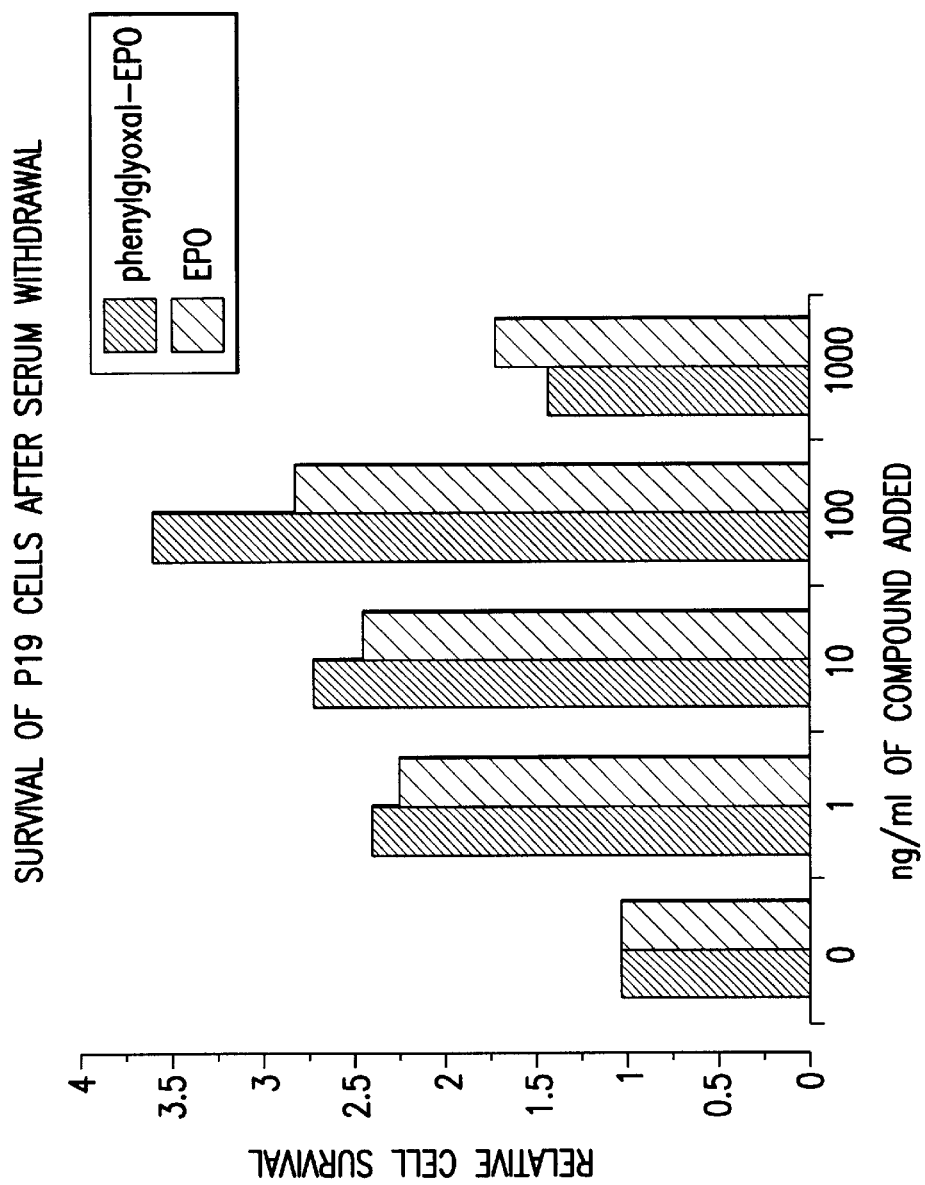
FIG. 5 compares the in-vitro efficacy of erythropoietin and phenylglyoxal-modified erythropoietin on the viability of serum-starved P19 cells.

Derivative EPOs desirable for the uses described herein may be generated by guanidination, amidination, trinitrophenylation, acetylation, succinylation, nitration, or modification of arginine residues or carboxyl groups, among other procedures, to produce erythropoietins which maintain their activities for specific organs and tissues but not for others, such as erythrocytes. When erythropoietin is subjected to the above reactions, it has been found that in general the resultant molecule lacks both in-vivo and in-vitro erythropoietic activity (e.g., Satake et al; 1990, *Biochim. Biophys.* Acta 1038:125–9). To test whether such modifications produce an EPO with preservation of its non-erythropoietic actions, such as neuroprotection, arginine residues were modified by using phenylglyoxal according to the protocol of Takahashi (1977, *J. Biochem.* 81:395–402) carried out for variable lengths of time ranging from 0.5 to 3 hrs at room temperature. The reaction was terminated by dialyzing the reaction mixture against water. The phenylglyoxal-modified EPO was tested using the neural-like P19 cell assay described above. As FIG. 5 illustrates, this chemically-modified EPO fully retains its neurotrophic effect.

EXAMPLE 6

Protection of Retinal Ischemia by Peripherally-administered EPO

Figure 6:
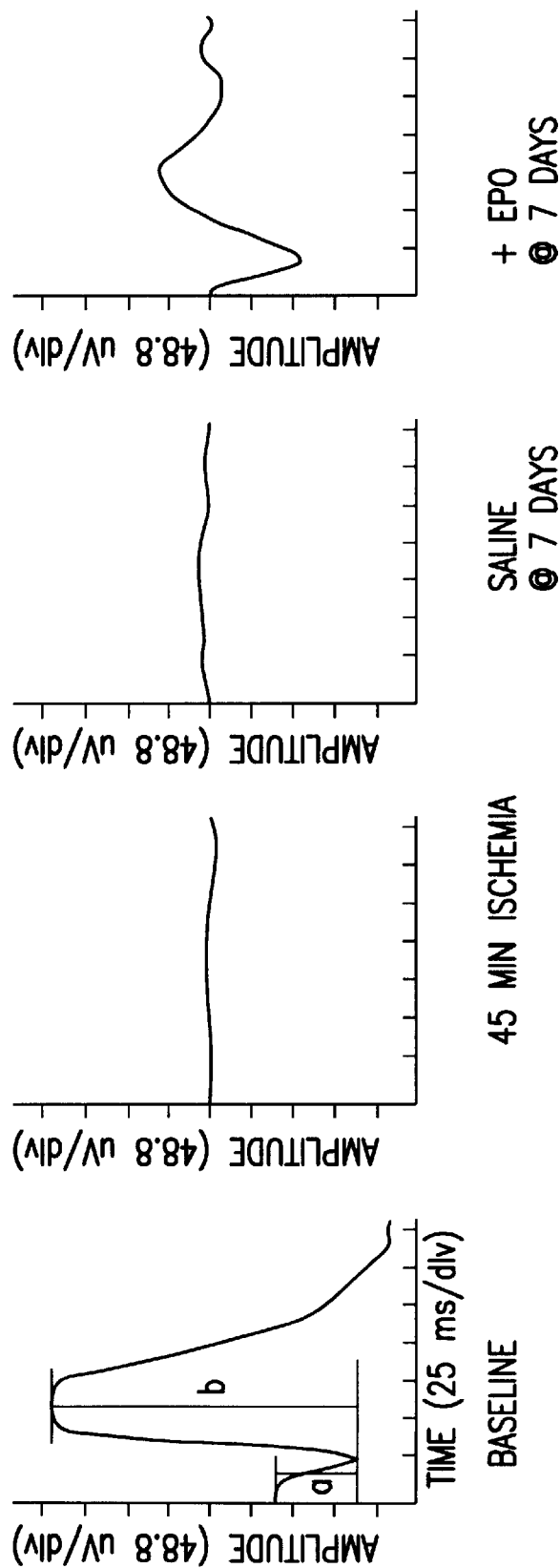
FIG. 6 depicts the effects of erythropoietin treatment in a rat glaucoma model.
Figure 7:
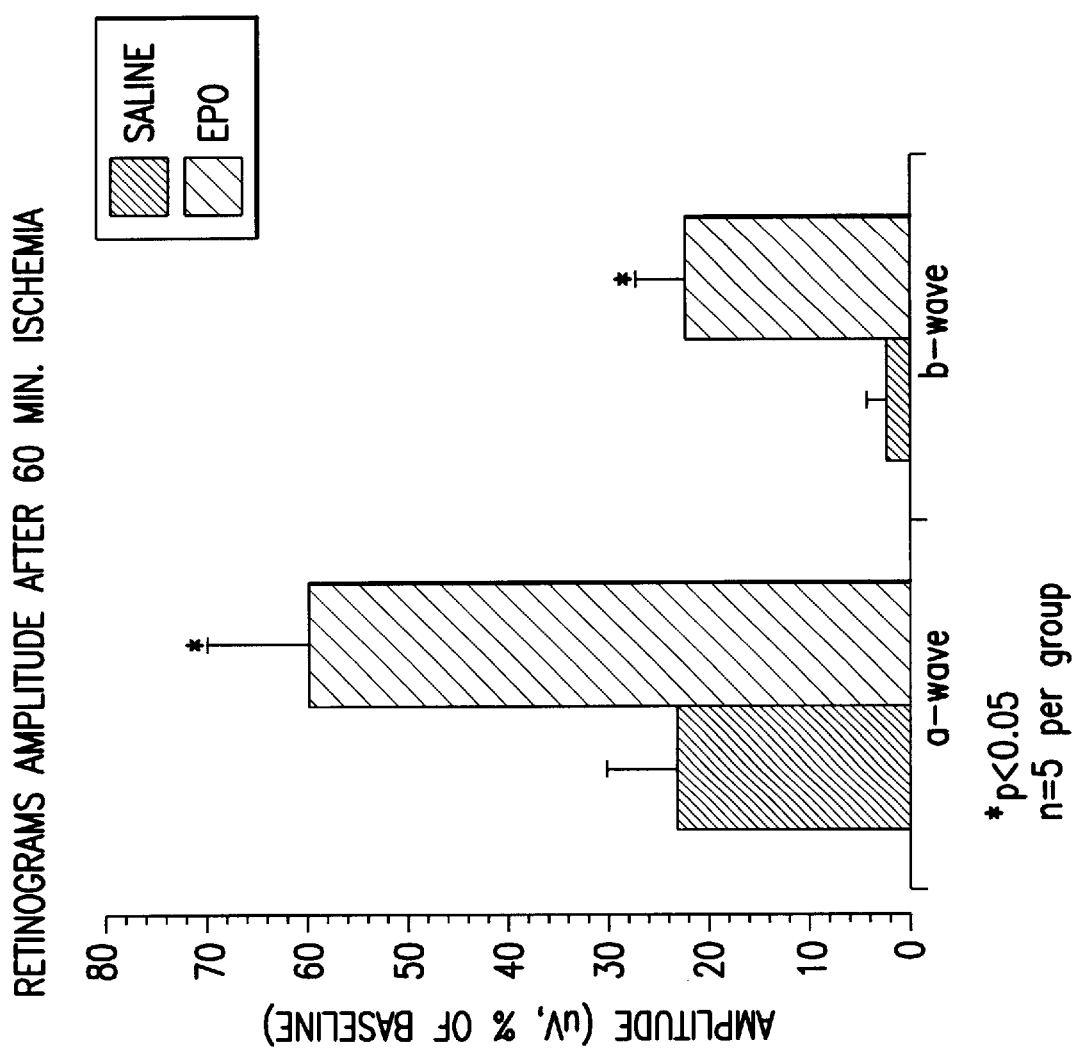
FIG. 7 shows the extent of preservation of retinal function by erythropoietin in the rat glaucoma model.

Retinal cells are very sensitive to ischemia such that many will die after 30 minutes of ischemic stress. Further, subacute or chronic ischemia underlies the deterioration of vision which accompanies a number of common human diseases, such as diabetes mellitus. At the present time there are no effective therapies to protect cells from ischemia. A tight endothelial barrier exists between the blood and the retina that excludes most large molecules. To test whether peripherally-administered EPO will protect cells sensitive to ischemia, an acute, reversible glaucoma rat model was utilized as described by Rosenbaum et al. (1997; *Vis. Res.* 37:3443–51). Specifically, saline was injected into the anterior chamber of the eye of adult male rats to a pressure above systemic arterial pressure and maintained for 60 minutes. Animals were administered saline or 5000 U EPO/kg body weight intraperitoneally 24 hours before the induction of ischemia, and continued as a daily dose for 3 additional days. Electroretinography was performed on dark-adapted rats 1 week after treatment. FIG. 6 illustrates that the administration of EPO is associated with good preservation of the electroretinogram (ERG) (Panel D), in contrast to animals treated with saline alone (Panel C), for which very little function remained. FIG. 7 compares the electroretinogram a- and b-wave amplitudes for the EPO-treated and saline-treated groups, and shows significant protection afforded by erythropoietin.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. A method for protecting or maintaining the viability of a cell, tissue or organ in a human being, said cell, tissue or organ comprising an erythropoietin-responsive cell or tissue, said cell, tissue or organ being separated from a vasculature in said human being by an endothelial cell barrier, said method comprising administering to said vasculature an amount of human asialoerythropoietin effective to translocate said endothelial cell barrier and protect or maintain said viability of said cell, tissue or organ.

2. A method for protecting or maintaining the viability of a CNS cell, tissue or organ in a human being, said CNS cell, tissue or organ being separated from a vasculature in said human being by an endothelial cell barrier, said method comprising administering to said vasculature an amount of human asialoerythropoietin effective to translocate said endothelial cell barrier and protect or maintain said viability of said CNS cell, tissue or organ.

3. A method for protecting or maintaining the viability of a retinal cell or tissue in a human being, said retinal cell or tissue being separated from a vasculature in said human being by an endothelial cell barrier, said method comprising administering to said vasculature an amount of human asialoerythropoietin effective to translocate said endothelial cell barrier and protect or maintain said viability of said retinal cell or tissue.

4. A method for protecting or maintaining the viability of a cell or tissue of the spinal cord in a human being, said spinal cord cell or tissue being separated from a vasculature in said human being by an endothelial cell barrier, said method comprising administering to said vasculature an amount of human asialoerythropoietin effective to translocate said endothelial cell barrier and protect or maintain said viability of said spinal cord cell or tissue.

5. A method for protecting or maintaining the viability of a heart cell or tissue in a human being, said heart cell or tissue being separated from a vasculature in said human being by an endothelial cell barrier, said method comprising administering to said vasculature an amount of human asialoerythropoietin effective to translocate said endothelial cell barrier and protect or maintain said viability of said heart cell or tissue.

6. A method for protecting or maintaining the viability of a cell, tissue or organ in a mammal, said cell, tissue or organ comprising an erythropoietin-responsive cell or tissue, said cell, tissue or organ being separated from a vasculature in said mammal by an endothelial cell barrier, said method comprising administering to said vasculature an amount of asialoerythropoietin effective to translocate said endothelial cell barrier and protect or maintain said viability of said cell, tissue or organ.

7. A method for protecting or maintaining the viability of a CNS cell, tissue or organ in a mammal, said CNS cell, tissue or organ being separated from a vasculature in said mammal by an endothelial cell barrier, said method comprising administering to said vasculature an amount of asialoerythropoietin effective to translocate said endothelial cell barrier and protect or maintain said viability of said CNS cell, tissue or organ.

8. A method for protecting or maintaining the viability of a retinal cell or tissue in a mammal, said retinal cell or tissue being separated from a vasculature in said mammal by an endothelial cell barrier, said method comprising administering to said vasculature an amount of asialoerythropoietin effective to translocate said endothelial cell barrier and protect or maintain said viability of said retinal cell or tissue.

9. A method for protecting or maintaining the viability of a cell or tissue of the spinal cord in a mammal, said spinal cord cell or tissue being separated from a vasculature in said mammal by an endothelial cell barrier, said method comprising administering to said vasculature an amount of asialoerythropoietin effective to translocate said endothelial cell barrier and protect or maintain said viability of said spinal cord cell or tissue.

10. A method for protecting or maintaining the viability of a heart cell or tissue in a mammal, said heart cell or tissue being separated from a vasculature in said mammal by an endothelial cell barrier, said method comprising administering to said vasculature an amount of asialoerythropoietin effective to translocate said endothelial cell barrier and protect or maintain said viability of said heart cell or tissue.

11. A method for enhancing cognitive or memory functions in a human being comprising peripherally administering an amount of human asialoerythropoietin effective to translocate a blood brain barrier and enhance the cognitive or memory function of the CNS.

12. A method for enhancing vision in a human being comprising peripherally administering an amount of human asialoerythropoietin effective to translocate a blood-eye barrier and enhance the visual function of a retinal cell or tissue.

13. A method for enhancing cardiac function in a human being comprising peripherally administering an amount of human asialoerythropoietin effective to translocate an endothelial cell barrier and enhance the cardiac function of a heart cell or tissue.

14. A method for enhancing motor or nerve function in a human being comprising peripherally administering an amount of human asialoerythropoietin effective to translocate an endothelial cell barrier and enhance the motor or nerve function of a spinal cord cell or tissue.

15. The method of any one of 1 or 2–14 wherein the amount of asiaolerythropoietin administered comprises 100 nanograms per kilogram up to about 50 micrograms per kilogram body weight.

16. A pharmaceutical composition comprising an effective non-toxic amount of asialoerythropoietin within the range from about 5 micrograms to 5 milligrams.

* * * * *